United States Patent [19]

Reisberg

[11] Patent Number: 5,468,242
[45] Date of Patent: Nov. 21, 1995

[54] FORM-FITTING MESH IMPLANT

[75] Inventor: Erhard Reisberg, Endingen, Germany

[73] Assignee: Leibinger Gmbh, Germany

[21] Appl. No.: 155,936

[22] Filed: Nov. 19, 1993

[51] Int. Cl.[6] .................................................. A61B 17/56
[52] U.S. Cl. .............................. 606/69; 606/60; 606/151
[58] Field of Search ............................... 606/1, 60, 69, 606/76, 77, 86, 105, 151, 213, 215, 216, 219, 220; 623/901

[56] References Cited

U.S. PATENT DOCUMENTS

| 1,105,105 | 7/1914 | Sherman | 606/69 |
|---|---|---|---|
| 2,580,821 | 1/1952 | Nicola | 606/69 |
| 4,502,161 | 3/1985 | Wall | 606/69 |
| 4,905,679 | 3/1990 | Morgan . | |
| 4,923,471 | 5/1990 | Morgan | 606/69 |
| 5,139,497 | 8/1992 | Tilghman et al. | 606/69 |
| 5,201,737 | 4/1993 | Leibinger et al. | 606/69 |

FOREIGN PATENT DOCUMENTS 0290138  11/1988  European Pat. Off. ................. 606/69

*Primary Examiner*—Stephen C. Pellegrino
*Assistant Examiner*—Glenn Dawson
*Attorney, Agent, or Firm*—Jones, Day, Reavis & Pogue

[57] ABSTRACT

A mesh grid implant of titanium or other biocompatible material having a plurality of orifice plate sections that accept bone screws and having curved connecting arms coupling each orifice plate section with each adjacent orifice plate section. The length of the curved arm and the included angle may be set to determine the flexibility of the mesh grid. The curved arms allow the mesh to cover not only flat bone segments but also to conform to curved, concave, and convex bone surfaces.

9 Claims, 3 Drawing Sheets

5,468,242

FORM-FITTING MESH IMPLANT

FIELD OF THE INVENTION

The present invention relates in general to a form-fitting mesh implant for the fixation and immobilization of bone fragments at one or more bone fracture sites, and in particular to a form-fitting mesh implant that accepts bone screws and has curved connecting bars or arms between the plate sections having the orifices for receiving the bone screws. The curved bars not only allow a surgeon to cover flat bone segments but also allow the surgeon to conform the mesh to curved bone surfaces, including concave, convex, or spherical surfaces for which the middle part of the mesh plate must be expanded significantly while the edges of the mesh plate are not expanded or may even be compressed. The bend in the connecting bars or arms allows them to be stretched to a much greater degree than a regular straight connecting bar of similar dimensions and strengths. The bend also allows the mesh to be compressed without creating overlapping or raised areas. The metals currently used for medical implants cannot be stretched to the degree required to shape a mesh sheet of the required thickness and strength to many of the convex and concave surfaces of the human anatomy, such as the skull. This invention creates such elasticity and formability through the design of the mesh in order to overcome the limitations of the material. Another method of fitting metal mesh plates or sheets to the convex skull shape is by cutting out wedges in the outer section of the plate to avoid overlapping sections when the plate is formed into a convex shape. This process is difficult and timeconsuming, and usually must be performed by the manufacturer prior to the operation. The present invention allows the mesh plate to be contoured to a concave or convex anatomical shape by the surgeon at the time of the operation.

BACKGROUND OF THE INVENTION

When there is a traumatic disruption of the continuity of a bone, it must be set such that there is no relative motion of the bone fragments at the fracture site during the healing process. If there is such relative movement, the surrounding tissues are irritated thus causing pain and requiting the time for fracture healing to be extended. Thus proper fixation and immobilization of bone fragments require an implant that can be molded or formed in substantially three dimensions in many cases, which is extremely difficult to accomplish. According to currently used techniques, if a mesh implant is used to cover the area of a lost craniotomy bone flap, the mesh, when formed or shaped, develops sides that overlap, turn upwardly, or create folds. Thus the current mesh systems overlap or curl when the mesh implant is shaped three dimensionally in order to adapt to a curved shape because the connecting bars or arms, that connect plate sections having orifices therein for receiving a bone screw, cannot be expanded and those at the outer edge cannot be compressed to a sufficient degree necessary to form a relatively smooth surface. Thus the overlapping edges and raised areas can cause lacerations of the overlying tissue that can result in infections.

Further, in the currently used techniques, reconstruction of the eye socket, including orbital walls, floor, and roof, is achieved with bone and alloplastic materials such as titanium plate implants to repair the defect. As an example, regular meshes or grid plates can be introduced and secured to the orbital rim with bone screws. Because of the variable radius of the eye sockets, a standard preformed implant usually will not fit precisely. The surgeon's task is to manually form the mesh implant so that the bone defect is covered in a manner such that the mesh material is formed to fit the original three-dimensional curvature of the bone. This is not achievable with conventional metal plate implants except to a limited extent with a grid plate that has separate sections or flaps that can be bent as a total section.

SUMMARY OF THE INVENTION

The present invention overcomes the disadvantages of the prior art by providing a mesh of titanium or other biocompatible material that has spaced orifice sections for accepting bone screws and has angled or curved connecting bars or arms between the spaced orifice sections for the bone screws. None of the prior art meshes has curved connecting bars. The purpose of the curved connecting bars is to allow a surgeon to cover flat bone segments as well as conforming the mesh to curved bone surfaces by either stretching, compressing, or curving the mesh implant. The angle in the connecting arms allows them to be stretched to a much greater degree than a regular straight connecting bar of similar dimensions and strengths or to be compressed if needed without causing overlapping sides, upward turning portions, or created folds that can cause both discomfort and lacerations of the overlying tissue. Thus the plate can be very easily contoured to a concave or convex anatomical shape by the surgeon at the time of operation, which is not true of a conventional mesh implant. In addition, this contouring can be done without distorting the bone screw holes in the spaced orifice sections because of the "stretching" and "compression" capacity of the curved connecting arms. The bone screw holes are countersunk to accept a bone screw with minimal protrusion of the screw head over the outer surface of the plate for less interference with the soft tissues covering the bone and less palpability. Thus the present invention avoids distortion of the screw holes, which is very important.

When the present invention is used to cover the area of a loss of a craniotomy bone flap, the mesh can be formed without the sides overlapping, turning upwardly, or creating folds.

Thus the present invention offers a mesh implant form that can be shaped in three dimensions much more easily and precisely by hand in the operating room. The curved arms of the present invention that connect at least two plate sections, each having an orifice therein for receiving a bone screw, are able to be stretched without deforming the screw hole. Depending on the screw hole pattern and considering the number of connecting arms, a three-dimensional level of stretching of the implant can be achieved by the use of various pressures. In one embodiment of the present invention, each orifice plate section has three substantially equally spaced curved connecting bars or arms that connect to three corresponding adjacent orifice plate sections. In another embodiment of the invention, four substantially equally spaced curved arms connect each orifice plate section with four corresponding adjacent orifice plate sections. In still another embodiment of the invention, two parallel curved arms connect each orifice plate section with each adjacent orifice plate section. If there are three connecting bars or curved arms, the arms must be made relatively stronger than where there are four connecting arms, and the curved arms may be more delicately made. The cross section profile of the connecting curved arm is substantially even over the entire length. However, the curved connecting arms in the area of the bend in the middle of the arm are slightly narrower in width in order that less force is needed to reach the desired final form of the implant by either compressing or expanding the arm. In other words, the connecting arms are somewhat wider at their junction with the orifice plate section and more narrow towards the middle of the arm in the area of the bend.

The smaller the included angle of the curved connecting arm between orifice plate sections and the longer the curved arm, the easier it is to manipulate the mesh implant so as to compress or expand the mesh as needed. Conversely, the greater the included angle and the shorter the curved arm, the smaller the capability to expand and compress the arm.

In the embodiment with two parallel connecting curved arms between any two orifice plate sections, the mesh requires more material and requires a greater amount of force to shape it. However the exertion required to shape the mesh implant will equal the three-dimensional stability of the mesh implant in its final form.

Thus it is an object of the present invention to provide a form-fitting mesh implant that has orifice plate sections that accept bone screws and that has curved connecting arms between the orifice plate sections.

It is still another object of the present invention to provide a form-fitting mesh implant that can be contoured to a concave or convex anatomical shape at the time of use of the mesh implant with the use of curved arms connecting spaced orifice plate sections that allow the connecting arms to be stretched or compressed as needed to form the desired anatomical shape.

It is yet another object of the present invention to provide a form-fitting mesh implant that has orifice plate sections that accept bone screws and has curved connecting arms between the orifice plate sections that could also be narrower in the middle than at the outer ends thereof in order to allow the arms to be more easily compressed or stretched in the area of the bend than a conventional straight connecting bar.

Thus the present invention relates to a form-fitting mesh implant for the fixation and immobilization of bone fragments at one or more bone fracture sites comprising a mesh of biocompatible metallic material having at least two plate sections with an orifice in each plate section for receiving a bone screw and at least one curved arm connecting the at least two plate sections and having a bend therein such that the arm can be selectively compressed, stretched, and contoured primarily at said bend to fixate bone fragments in a particular anatomical shape without deformation of the bone screw orifices.

BRIEF DESCRIPTION OF THE DRAWINGS

These and other objects of the present invention will be more fully disclosed when taken in conjunction with the following DETAILED DESCRIPTION OF THE DRAWINGS in which like numerals represent like elements and in which.

DETAILED DESCRIPTION OF THE DRAWINGS

Figure 1:
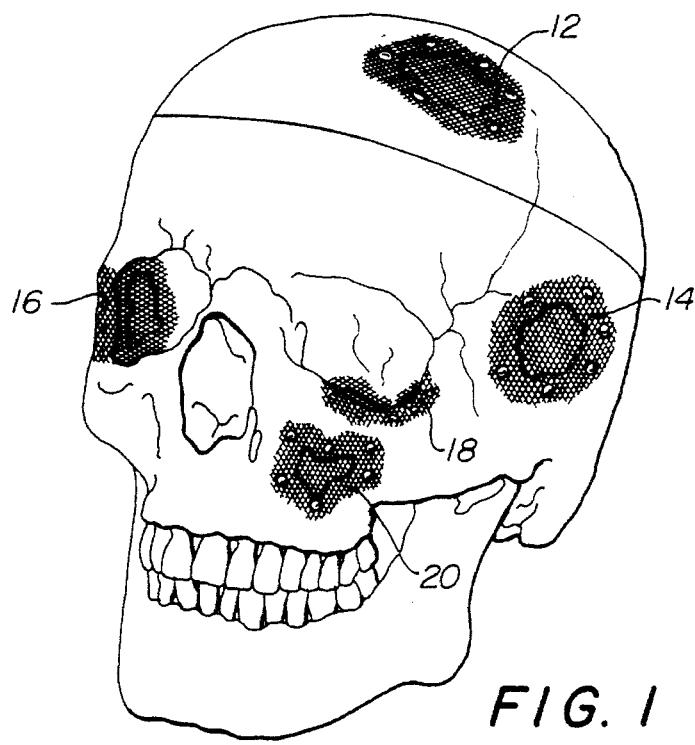
FIG. 1 is a representation of a human skull illustrating representative anatomical portions thereof that can be repaired with the mesh implant of the present invention.

FIG. 1 is a representation of a skull illustrating representative areas where traumatic disruption of the continuity of bone can occur. At location 12 on the top of the skull, a fracture or bone fragment must be repaired or a gap in the bone bridged. On the left side of the skull, an area 14 around the ear must be repaired or bridged. On the outside 16 of the right eye, a bone fracture is to be repaired. The floor 18 of the left eye socket is shown as an area that can be repaired and a bone fracture or gap in the cheek bone area 20 below the left eye is also shown with the mesh implant so that it can be repaired. In all of these cases, a biocompatible metallic mesh is used for defect-bridging reconstruction of bony structures or to stabilize fractured elements and to facilitate the growing together of the bone in the affected area. These areas all have different contours and shapes and thus the mesh implant that is used must be contoured for the particular area. Thus in the area 12, the mesh must have a slight spherical shape. In the area 16 around the right eye, the mesh implant must have a number of shapes including convex, concave, and slightly hemispherical. In all of these cases, the mesh implant must be shaped to conform anatomically to the area where the mesh is being used.

Figure 2:
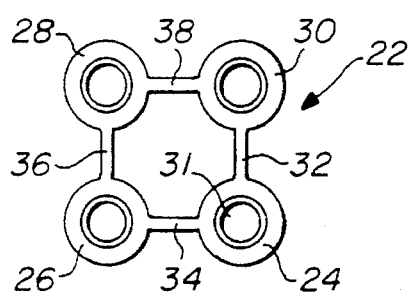
FIG. 2 is a diagram of a mesh implant arrangement disclosed in a prior copending application.

FIG. 2 illustrates a mesh implant disclosed in copending and commonly assigned U.S. application Ser. No. 08/004, 220, filed Jan. 11, 1993, in which the mesh 22 has orifice plates 24, 26, 28, and 30, each having an orifice 31 therein for receiving a bone screw. The orifices 24, 26, 28, and 30 are connected by straight arms 32, 34, 36, and 38 to form a substantially rectangular grid. However, other shapes are also formed such as triangular, octagonal, and the like. However, in each case the connecting arms are straight as shown in FIG. 2. Clearly, such mesh implant could be made in whatever size or dimensions desired by extending the design shown in FIG. 2. In order to shape an implant formed of the mesh of the prior art such as that illustrated in FIG. 2, it is sometimes required to shape the mesh such that sides overlap, turn upwardly, or create folds. Such overlapping or turned up edges or folds can cause lacerations of the overlying tissue which can result in substantial pain, in infections, and in difficulty of healing.

Figure 3:
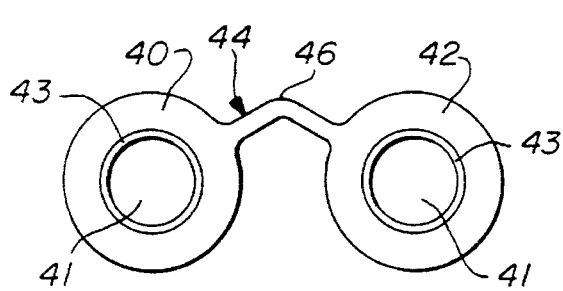
FIG. 3 is a diagram of a mesh implant arrangement of the present invention wherein two orifice plate sections are connected by a curved arm.
Figure 4:
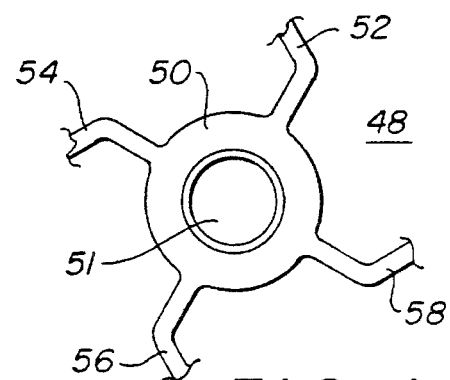
FIG. 4 is an illustration of an orifice plate section having four equally spaced curved arms extending therefrom.

The concept of the present invention is illustrated in FIG. 3 and comprises a mesh formed of spaced orifice plate sections 40 and 42, each of which has an orifice 41 for receiving a bone screw and wherein the orifice plate sections 40 and 42 are connected by a curved connecting arm 44 having a bend 46 substantially in the middle thereof. Such bend 46 allows the two orifice plate sections 40 and 42 to be easily moved towards and away from each other without substantially deforming the connecting arm 44 except by changing the included angle 45 of the bend 46. Thus it can be stretched or compressed without overlapping or curling of the material upwardly or creating folds. The orifice plate sections 40 and 42 are countersunk at 43 to accept the bone screw with minimal protrusion of the screw head over the outer surface of the mesh plate formed therewith for less interference with the soft tissues covering the bone and less palpability. Thus by compressing or stretching curved arm 46, distortion of the screw holes 41 is avoided, which is very important when these meshes must be contoured t,o a particular anatomical structure. FIG. 4 illustrates a particular construction 48 of an orifice plate 50 having four substantially equally spaced curved arms 52, 54, 56, and 58 thereon.

Figure 5:
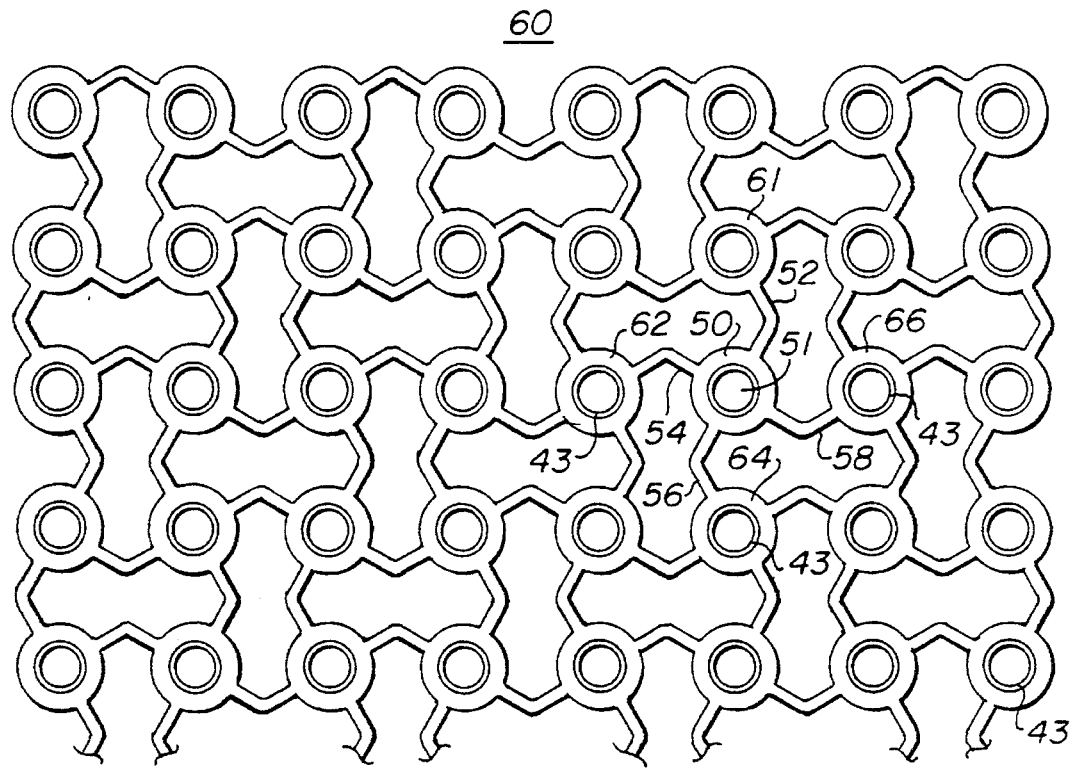
FIG. 5 is a diagram of a mesh implant section of the present invention utilizing the orifice plate sections with four curved arms as illustrated in FIG. 4.

FIG. 5 illustrates a form-fitting mesh implant grid system 60 that is constructed from the plurality of orifice plate sections 50 as illustrated in FIG. 4. Note in FIG. 5 that orifice plate section 50 is coupled with curved arm 52 to adjacent orifice plate section 61, to adjacent orifice plate section 62 through curved arm 54, to adjacent orifice plate section 64 through curved arm 56, and to adjacent orifice plate section 66 with curved arm 58. All of the other orifice plate sections illustrated in FIG. 5 are coupled in a similar manner to each other through four equally spaced curved arms. Such construction allows the mesh implant system 60 to be formed into various anatomical shapes by either stretching, compressing, or bending the curved arms to form a desired anatomical shape. Thus this mesh could be used as illustrated in FIG. 1 for any of the mesh shapes and the desired size can be cut from the mesh implant screen or grid system 60 and then can be easily shaped at the time of the operation to form the desired anatomical shape.

Figure 6:
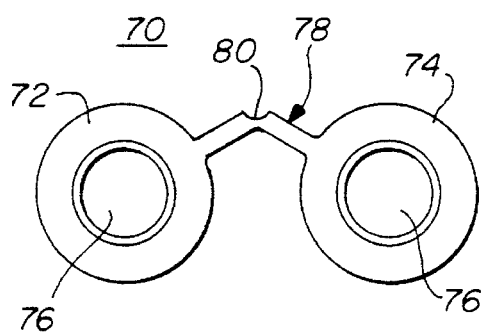
FIG. 6 is an illustration of another embodiment of the present invention in which two orifice plate sections are coupled by a curved arm that is widest at the junction of the arm with the orifice plate section and narrowest in the middle of the curved arm.
Figure 7:
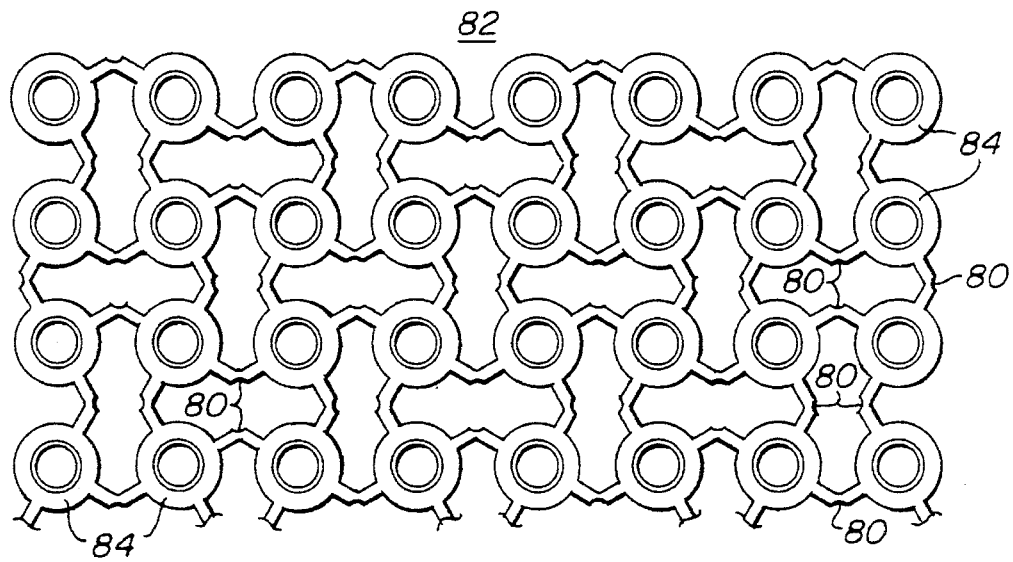
FIG. 7 is a diagram of a mesh implant arrangement using the embodiment illustrated in FIG. 6 in which each connecting curved arm has a middle section that is narrower than the junction of the arm with the orifice plate section.

FIG. 6 illustrates another important embodiment of the present invention illustrating a mesh grid construction 70 wherein the first and second orifice plate sections 72 and 74 having orifices 76 therein are joined by a curved arm 78 having a narrower section 80 at the center thereof than in the area where the arm 78 joins the orifice plate sections 72 and 74. This thinner section 80 allows easier shaping and molding of a mesh implant system created with such mesh construction 70. FIG. 7 illustrates such a mesh construction 82. Thus the entire mesh construction 82 of FIG. 7 can be easily cut to a predetermined size and then molded to assume a predetermined anatomical structure shape by stretching, compressing, and bending the curved arms as desired without distorting the orifices 76.

Figure 8:
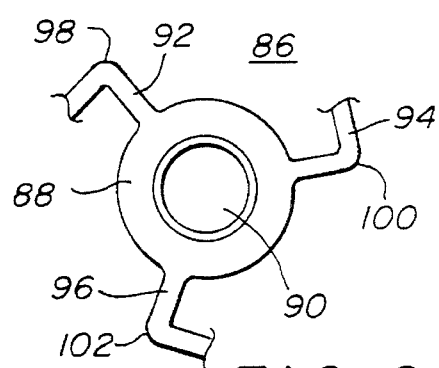
FIG. 8 is a diagrammatic representation of still another embodiment of the present invention in which the orifice plate section has three substantially equally spaced cur,red arms extending therefrom.
Figure 9:
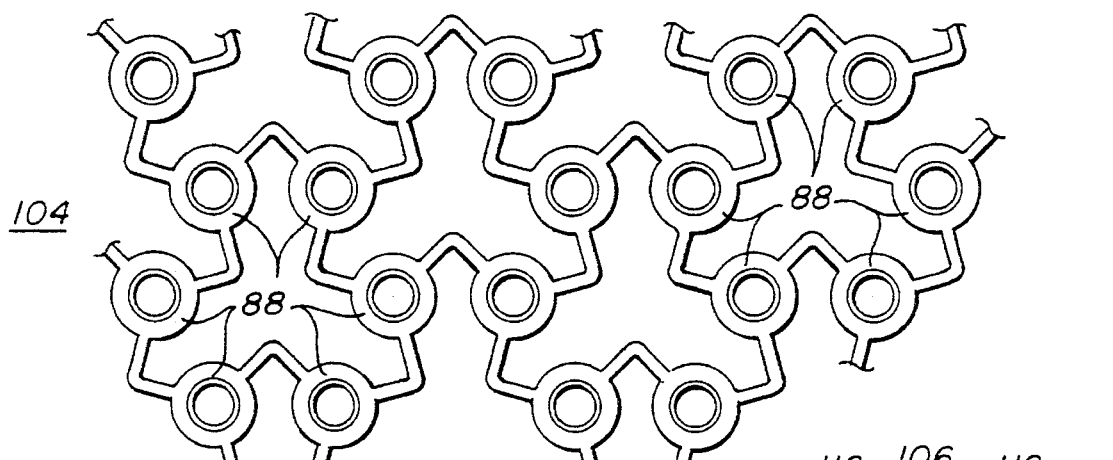
FIG. 9 is an illustration of a mesh implant arrangement utilizing the orifice plate section of FIG. 8 with the three curved connecting arms extending therefrom.

The alternate embodiment 86 illustrated in FIG. 8 includes an orifice plate section 88 having an orifice 90 and three substantially equally spaced depending arms 92, 94, and 96 that are curved at 98, 100, and 102, respectively. The mesh grid system 104 illustrated in FIG. 9 incorporates the embodiment of FIG. 8 and illustrates each orifice plate section 88 on the interior of the mesh system 104 being coupled to each adjacent orifice 88 by a curved arm as illustrated. On the outer periphery of the mesh 104, the orifice plate sections are coupled only to two adjacent orifice plate sections as shown.

Figure 10:
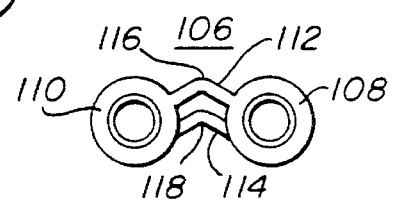
FIG. 10 is an illustration of still another embodiment of the present invention wherein two orifice plate sections are connected by two parallel curved arms.
Figure 11:
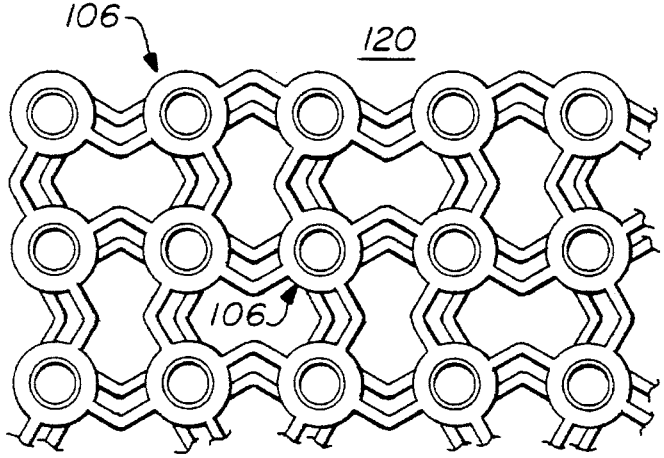
FIG. 11 is an illustration of an alternate mesh implant arrangement utilizing the embodiment of FIG. 10 wherein each orifice plate section is connected to an adjacent orifice plate section with two parallel curved connecting arms.

FIG. 10 illustrates still another embodiment 106 of the present invention in which orifice plate sections 108 and 110 are coupled to each other by parallel spaced bent arms 112 and 114 having bends 116 and 118 therein respectively. The use of this version in a mesh grid system or screen 120 is illustrated in FIG. 11 wherein each of the interior orifice plate sections 106 is coupled to an adjacent orifice plate section by means of a pair of parallel spaced curved arms as illustrated. This implant requires more material and would require a greater amount of force to shape it as opposed to the embodiments illustrated in FIG. 5, FIG. 7, and FIG. 9. However, the exertion required to shape the mesh screen 120 in FIG. 11 will equal the three-dimensional stability of the mesh implant formed with screen 120 in its final form.

Figure 12:
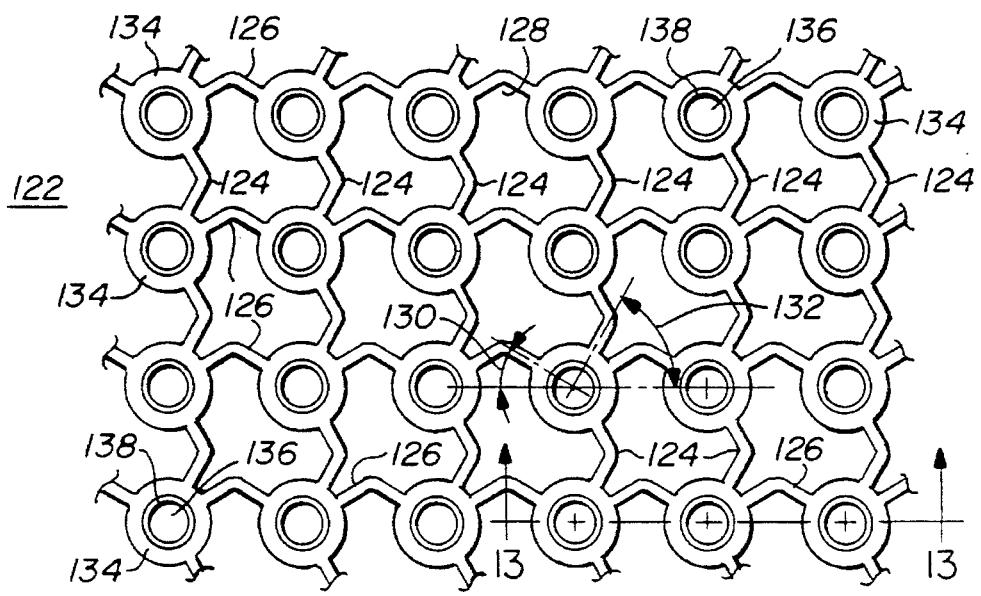
FIG. 12 is a plan view of still another embodiment of the present invention.

FIG. 12 is a plan view of still another embodiment of the present invention and includes a grid section 122 of a form-fitting mesh implant for the fixation and immobilization of bone fragments and bridging of bone defects that is again formed of biocompatible metallic material having a plurality of plate sections 134 with an orifice 136 in each plate section for receiving a bone screw. Again, at least one curved arm 124 and 126 connects each two adjacent plate sections 134. Again, each of the arms 124 and 126 has a bend therein such that the curved arms 124 and 126 can be selectively compressed, stretched, and contoured without deformation of the bone screw orifice 136. It will be noted in this case that all of the rows of curved arms 124 are all bent in the same direction and that all of the column curved arms 126 are also bent in the same direction. This construction allows the mesh implant to be more readily compressed or stretched in any given direction. For instance, if the entire mesh implant section 122 shown in FIG. 12 needed to be compressed in the horizontal direction in FIG. 12, all of the curved arms 126 could be compressed all in the same direction. In like manner, if the mesh implant 122 needed to be compressed in the vertical direction, all of the curved arms 124, in either one row or in all rows, could be compressed. Thus with such construction, the mesh implant 122 can be readily shaped by compressing, stretching, and contouring in whatever direction is needed to form the shape needed for a particular bone configuration. It will be noted in FIG. 12 that the included angle of the curved arms 124 and 126 may be, for example, 120°. In like manner, the angle of the curved arm 124 and 126 as it exits from the orifice plate may be, for example only, 30° as illustrated by the numeral 130. The angle the curved arm 124 makes with the horizontal as it exits the orifice plate 134 may be 60°, for example, as illustrated by the numeral 132. Orifices 136 have a sloping shoulder 138 so that the bone screws having a corresponding sloping shoulder have a minimum projection above the grid or mesh implant 122.

Figure 13:
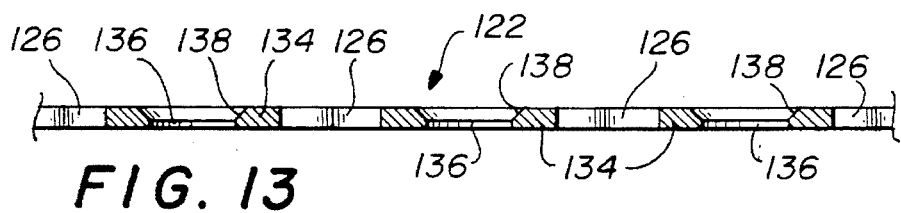
FIG. 13 is a cross-sectional view of the embodiment of FIG. 12.

FIG. 13 is a cross-sectional view of the mesh implant 122 illustrating that the curved arms 126 are 0.3 millimeter in thickness, for example, the diameter of the upper portion of the orifice 136 is 1.55 millimeters while the diameter of the lower portion of the orifice is 1.2 millimeters, and the thickness of the orifice plate 134 is shown to be, for example only, 0.42 millimeter. The radius of an orifice plate 134 may be, for example only, 1.25 millimeters and the width of a curved arm may be, for example only, 0.3 millimeter. As those skilled in the art will appreciate, other size configurations could be used and the preceding explanation is for illustrative purposes only.

Thus, there has been disclosed a novel three-dimensional form-fitting mesh implant which may be formed of titanium or other biocompatible material and that has plate sections with orifices that accept bone screws and that are connected to each other with curved connecting arms. The purpose of the curved connecting arms is to allow a surgeon to cover flat bone segments as well as to conform the mesh to curved bone surfaces. The bend in the connecting arms allows them to be stretched to a far greater extent than a regular straight connecting bar of similar dimensions and strengths may be stretched. Also, the curved arm can be easily compressed without the sides overlapping, turning upwardly or creating folds. Thus a mesh implant plate can be contoured to a concave or convex anatomical shape by the surgeon very easily at the time of the operation. In addition, this contouring can be done without distorting the screw holes because of the "stretching" and "compression" capacity of the curved connecting arms.

In one embodiment, each orifice plate section is coupled to three adjacent orifice plate sections with a curved arm. In another embodiment, each orifice plate section is coupled to each of four adjacent orifice plate sections with one of the curved arms. In still another embodiment of the invention, the curved arms are narrower at the center thereof than at the outer ends where they join the orifice plate sections to allow easier stretching and compression of the curved arms. In still another version of embodiment of the present invention, at least two parallel curved arms connect each orifice plate section to each adjacent orifice plate section.

Figure 14:
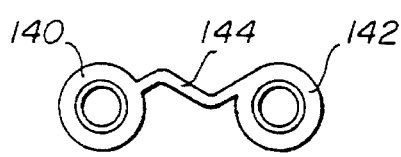
FIG. 14 is an illustration of another embodiment of the present invention.

In a still further embodiment of the present invention, as shown in FIG. 14, orifice plate sections 140 and 142 are coupled together by a curved arm 144 having two curves rather than one curve as shown in the other embodiments. As those skilled in the art will appreciate other numbers of curves could be incorporated into the implant between orifice plate sections.

Figure 15:
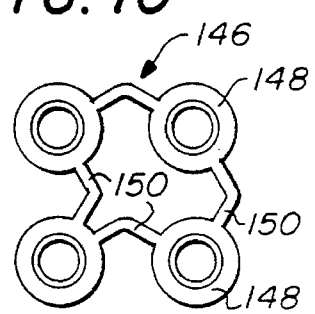
FIG. 15 is an illustration of a still further embodiment of the present invention.

Finally, FIG. 15 discloses another embodiment of the present invention, namely, a single rectangular grid 146 formed by four orifice plates 148 coupled to curved arms 150.

While the invention has been described in connection with particular structural embodiments of the mesh having orifice plate sections that accept bone screws and having curved connecting arms between the orifice plate sections, many modifications of the invention will be apparent to those skilled in the art and, accordingly, such modifications are to be included within the spirit and scope of the invention as defined in the following claims.

I claim:

1. A form-fitting mesh implant for the fixation and immobilization of bone fragments and bridging of bone defects or gaps at one or more sites of a patient including:

a mesh of biocompatible metallic material having a plurality of plate sections forming a grid with an interior area and an exterior periphery;

an orifice in each plate section for receiving a bone screw; and four arms integrally formed with each plate section in the interior area, each arm having at least two arm sections connected at a bend and connecting a plate section in the interior area with an adjacent plate section such that the arm can be selectively compressed, stretched, and contoured primarily by deformation at said bend to fixate bone fragments in a particular anatomical shape.

2. A form-fitting mesh implant as in claim 1 wherein each arm further includes:

a first width at the connection of the arm with a plate section; and a second smaller width in substantially the bend in the arm such that pressure applied to the mesh will change the shape of the mesh substantially only at the bends of the arms.

3. A form-fitting mesh implant as in claim 1 further including:

an included angle formed by said bend in said arm; and said arm having a given length connecting plate sections such that the greater the length of the arm and the smaller the included angle, the greater the expansion and compression capabilities of said mesh and the smaller the length of the arm and the greater said included angle, the lesser the expansion and compression capabilities of said mesh.

4. A form-fitting mesh implant as in claim 1 wherein at least one of said arms includes more than one bend.

5. A form-fitting mesh implant for the fixation and immobilization of bone fragments and bridging of bone defects or gaps at one or more sites of a patient comprising:

a mesh of biocompatible metallic material having a plurality of plate sections forming a grid with an interior area and an exterior periphery;

an orifice in each plate section for receiving a bone screw; and three arms integrally formed with each plate section in said interior area, each arm connecting each plate section in said interior area with an adjacent plate section; and each of said arms having at least two arm sections connected at a bend such that the arm can be selectively compressed, stretched, and contoured primarily by deformation at said bend to fixate bone fragments in a particular anatomical shape.

6. A form-fitting mesh implant as in claim 5 wherein at least one of said arms includes more than one bend.

7. A form-fitting mesh implant for the fixation and immobilization of bone fragments and bridging of bone defects or gaps at one or more sites of a patient including:

a mesh of biocompatible metallic material having a plurality of plate sections with an orifice in each plate section for receiving a bone screw, said plate sections forming a mesh grid with an interior area and an exterior periphery; and at least two parallel arms connecting each interior area plate section with each adjacent plate section, each of the parallel arms having at least two arm sections connected at a bend such that the arm can be selectively compressed, stretched, and contoured primarily by deformation at said bend to fixate bone fragments in a particular anatomical shape.

8. A form-fitting mesh implant for the fixation and immobilization of bone fragments and bridging of bone defects or gaps at one or more sites of a patient including:

a mesh of biocompatible metallic material having a plurality of plate sections arranged in a lattice-like structure of rows and columns, each plate section having an orifice for receiving a bone screw;

an arm connecting adjacent ones of said plate sections in each row and connecting adjacent ones of each plate section in each column, each arm having at least two arm sections connected at a bend such that the arm can be selectively compressed, stretched, and contoured primarily by deformation at said bend to fixate bone fragments in a particular anatomical shape; and all of said arms connecting said rows of plate sections being bent in the same direction and all of said arms connecting said columns of plate sections being bent in the same direction.

9. A form-fitting mesh implant as in claim 8 wherein at least one of said arms includes more than one bend.

* * * * *